United States Patent [19]

Fernwood et al.

[11] Patent Number: 4,493,815
[45] Date of Patent: Jan. 15, 1985

[54] SUPPORTING AND FILTERING BIOCHEMICAL TEST PLATE ASSEMBLY

[75] Inventors: George G. Fernwood, San Anselmo; Samuel Burd, Oakland, both of Calif.

[73] Assignee: Bio-Rad Laboratories, Inc., Calif.

[21] Appl. No.: 518,231

[22] Filed: Jul. 28, 1983

[51] Int. Cl.³ .................... B01D 25/04; G01N 33/48
[52] U.S. Cl. .................................. 422/101; 436/177; 210/232; 210/450; 210/455
[58] Field of Search .................. 422/58, 102, 104, 101, 422/46, 48; 436/177, 178, 807, 808, 809; 435/287, 293, 300; 210/332, 450, 455, 456

[56] References Cited

U.S. PATENT DOCUMENTS

| | | | |
|---|---|---|---|
| 3,378,347 | 4/1968 | Saravis | 422/58 |
| 3,378,481 | 4/1968 | Saravis et al. | 204/299 |
| 3,389,966 | 6/1968 | Saravis | 422/58 |
| 3,390,962 | 7/1968 | Goldsmith | 422/58 |
| 3,554,704 | 1/1971 | Ushakoff | 436/809 |
| 3,730,352 | 5/1973 | Cohen et al. | 210/332 |
| 3,990,852 | 11/1976 | Piazzi et al. | 422/102 |
| 4,012,198 | 3/1977 | Finter et al. | 435/7 |
| 4,031,197 | 6/1977 | Marinkovich | 424/1 |
| 4,039,247 | 8/1977 | Lawman et al. | 350/95 |
| 4,090,850 | 5/1978 | Chen et al. | 422/102 |
| 4,246,339 | 1/1981 | Cole et al. | 435/7 |
| 4,371,624 | 2/1983 | Saxholm | 435/291 |

OTHER PUBLICATIONS

"Minifold, Micro—Sample Filtration Manifold", Schleicher & Schuell Bulletin No. 358, Keene, N.H., 1981.
Drawings of Harvard Filter Assay Device—Plate A, Plate B, Plate C.

*Primary Examiner*—Barry S. Richman
*Assistant Examiner*—Joseph P. Carrier
*Attorney, Agent, or Firm*—Townsend and Townsend

[57] ABSTRACT

A biochemical test plate assembly is disclosed for use in both filter assays and fluid retention applications. The assembly comprises an upper template with a plurality of discrete apertures, a continuous microporous film underlying the upper template, a gasket underlying the microporous film with apertures matching those of the upper template, a lower template underlying the gasket with a similar array of apertures matching those of both the upper template and the gasket, each aperture terminating at its upper end in a flat boss, and a base plate having a central recess to define an enclosed chamber when the base plate and lower template are in contact, the base plate being designed to form an air-tight seal between it and the lower template.

5 Claims, 8 Drawing Figures

SUPPORTING AND FILTERING BIOCHEMICAL TEST PLATE ASSEMBLY

BACKGROUND OF THE INVENTION

1. Field of the Invention

The present invention relates to an apparatus for biochemical testing and screening and for the performance of biochemical reactions in general. In particular, this invention relates to a dual purpose multicell device, suitable for both (a) drawing a fluid containing biochemical species through a microporous membrane, and (b) supporting a static fluid above such a membrane for an indefinite length of time.

2. Description of the Prior Art

Microtiter wells are used in biochemical laboratories for a multitude of functions, including recombinant DNA screening, hybridoma screening, and immunoassays such as the radioimmunoassay (RIA), enzyme linked immunosorbent assays (ELISA), enzymoimmuno assays (EIA), and enzyme multiplied immunoassay techniques (EMIT).

One of the known designs in current use is a multiwell plate assembly containing a binding or support matrix in the form of a planar membrane forming the bottom surface of each well. This is useful for a variety of biochemical procedures, including identification, isolation, concentration and purification of various types of species. One example is the flow-through contact between a first reactant mobile in the fluid phase and a second reactant immobilized on the support matrix. Another example is the combination of two or more reactants in the liquid phase to form a complex during prolonged retention of the fluid above the membrane, followed by drawing of the fluid and uncomplexed reactants down through the membrane to filter out the larger complex. A further example is the prolonged incubation of antibody-secreting cells or the like, followed by drawing of the surrounding fluid containing the antibodies or other selected products down through the membrane. Further procedures or combinations of the above to which this design is suitable are well known to those skilled in the art. In generalized terms, this type of assembly in order to accommodate the full range of these procedures must be capable of both retaining a fluid in the well above the membrane without substantial leakage downward beyond permeating the membrane itself, and drawing a fluid down through the membrane when desired as by negative pressure.

One example of this known design is a multiwell test plate comprised of a combination of parallel plates with holes extending therethrough according to the standard microtiter well spacing, and a flexible membrane clamped between the plates in a sandwich-type configuration. The wells are thus defined by the holes in the uppermost plate, the upper membrane surface forming the bottom of each well.

The structures currently known are characterized by uneven and unreliable sealability between the wells, poor uniformity of contact area on the membrane from one well to the next, and a lack of versatility in being able to perform both functions mentioned above. The lateral leakage and lack of uniform contact areas is a particularly serious failing since it obscures the test results when instrumentation such as a scanning densitometer is used for quantitation, by providing false or distorted readings and a high level of background counts. Even without the use of a scanning densitometer, absolute errors are often introduced by irregularities in the accessible membrane area from one well to the next. For example, in assays where one binding species is covalently bound to the membrane and the other is mobile, variations in the accessible membrane area will cause unwanted variations in the amount of the species covalently bound.

SUMMARY OF THE INVENTION

A biochemical test plate assembly for use in performing each of the two functions described above is provided herein. The assembly overcomes the disadvantages of similar items presently known and provides accuracy in measurement and versatility in use. Specifically, it has now been discovered that a test plate assembly having these beneficial features is one comprised of an upper plate with a plurality of apertures (template), a microporous film underlying the upper plate, a gasket underlying the microporous film with apertures in alignment with those of the upper plate, a lower plate with a similar array of apertures each terminating at its upper end in a flat boss, a base plate having a central recess which defines an enclosed chamber when the base plate and lower template are in contact, and a vacuum connection to the base plate recess. An air-tight seal is formed between the lower template and base plate, and the parts are secured together under a tension sufficient to cause the gasket to seal the periphery of each aperture against lateral leakage.

DETAILED DESCRIPTION OF THE DRAWINGS AND PREFERRED EMBODIMENTS

The test plate assembly of the present invention is designed to provide a plurality of discrete wells or reservoirs arranged in a horizontal array to permit a multitude of biochemical tests to be run simultaneously. The number, size, and spacing of the wells will preferably conform to the format of typical laboratory equipment used in biochemical laboratories. One example is the well spacing in the Microtiter ® dish of Dynatech Corporation. Use of this or a similar well format will permit the use of the test plate assembly in conjunction with standardized equipment such as automated scanning densitometers and automated well washing equipment. The typical array will comprise 96 circular wells in an 8-by-12 rectangular array, with a center-to-center spacing of approximately 9 mm. Other examples include oval- or slot-shaped wells with associated apertures of appropriate shape.

Figure 1:
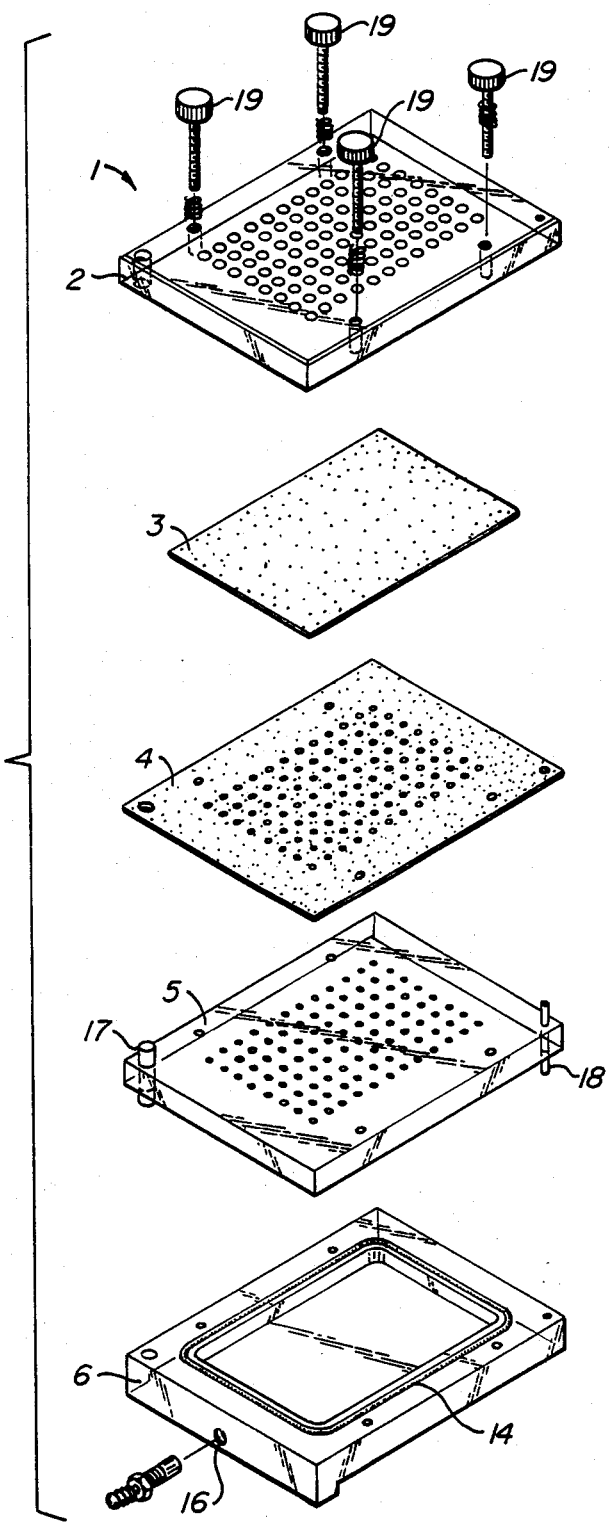
FIG. 1 is an expanded view of one embodiment of a test plate assembly according to the present invention.

FIG. 1 illustrates an embodiment of the test plate assembly of the invention, as designed for a 96-well array of cylindrical wells. The assembly is designated by the numeral 1, its primary parts consisting of an upper template 2, a microporous membrane 3, a gasket 4, a lower template 5 and a base plate 6.

Figure 2A:
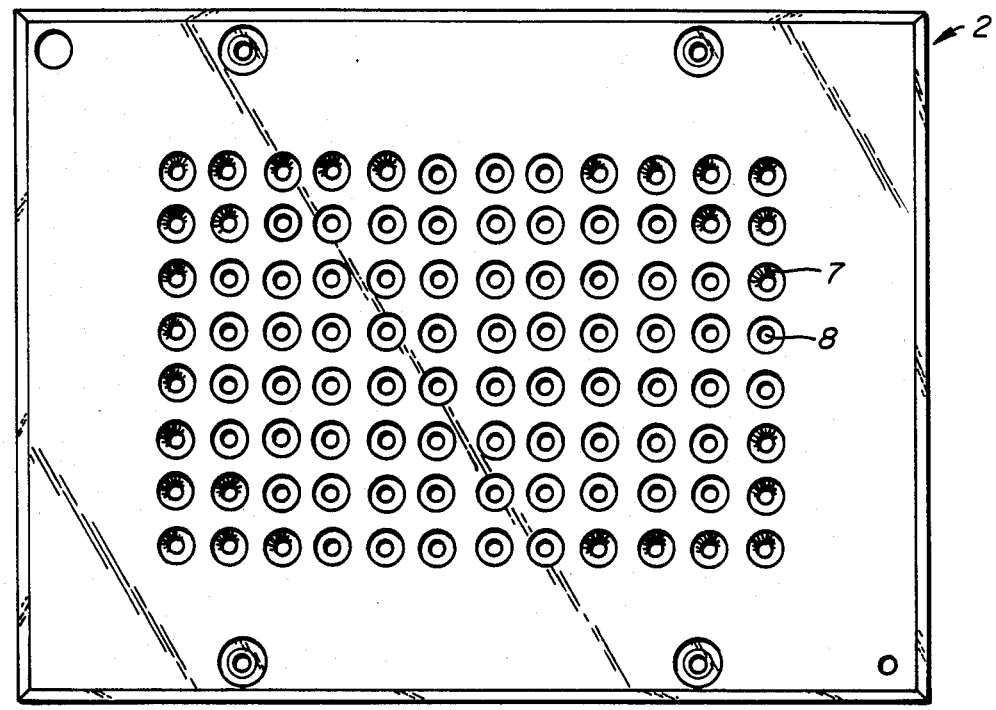
FIG. 2A is a plan view and FIG. 2B is an end view of an upper template for use in the embodiment of FIG. 1.
Figure 2B:
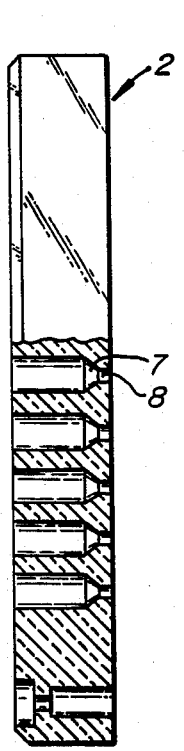

FIG. 2 illustrates the upper template in detail. In the embodiment shown, the diameter of each well undergoes a reduction from the upper surface of the plate to the lower surface. Such a size reduction is useful in concentrating the biochemical species as it passes through the well and is deposited on the microporous membrane, improving the ease of detection in subsequent processing steps. The extent of diameter reduction will determine the degree of concentration, and is likewise not a critical feature of this embodiment. The degree of reduction is limited in some cases by the need to leave a sufficient binding area accessible for the sample to produce detectable results. In other cases such as, for example, where binding does not occur on the matrix itself but the latter is used strictly for filtering purposes, the degree of reduction will be less limited. An example of the latter type of assay is one involving complex formation between mobile species in the fluid phase, where the membrane operates as a filter to separate the larger complex from the uncomplexed species. The sensitivity of the assay will depend on the amount of complex formed in relation to the accessible membrane area, and thus the greater the diameter reduction, the greater the sensitivity of the assay. Taking all these considerations into account for most applications a final diameter (after reduction) within the range of about 0.1 cm to about 0.5 cm will provide the best results.

The diameter reduction is preferably achieved by including a tapering portion 7 in each aperture, having angled sides to permit complete drainage of the fluid toward the bottom of the well. To maximize the well capacity, the tapering portion is located toward the base of the aperture. The well capacity is not critical, however, and can vary over a wide range. Typical wells will fall within the range of about 100 to about 1,000 microliters in volume.

A further feature of each aperture in this embodiment is a straight (constant diameter) portion 8 below the tapered portion. The straight portion improves quality control during the manufacturing of the plate, by improving the uniformity of the diameter at the lower surface opening from one aperture to the next. This helps to provide a uniform contact area on the microporous membrane across the entire array of wells. The straight portion also helps to prolong the useful life of the apparatus by minimizing the risk of chipping.

The microporous membrane 3 is placed immediately below the upper template. The membrane may be constructed of any medium capable of immobilizing a biochemical species, including antigens, antibodies, conjugates, blocking agents, cells, precipitates, and others. The appropriate medium will depend on the type of species and type of immobilization desired. The latter may include adsorptive immobilization, covalent immobilization, anionic immobilization, precipitate entrapment, or cell entrapment, as examples. Suitable media include such materials as nitrocellulose, diethylaminoethyl cellulose, mylar, nylon, cellulose acetate, and glass fiber. Other suitable materials will be apparent to those skilled in the art.

Neither the pore size of the membrane nor the membrane thickness are critical. Both can vary widely depending on the type of species and type of immobilization desired. In most applications, pores of diameter ranging from about 0.001 to about 1.0 micron, preferably from about 0.005 to about 0.5 micron in diameter, and membrane thicknesses of about 0.1 to about 1,000 microns, preferably from about 1 to about 100 microns, will provide the best results.

Figure 3:
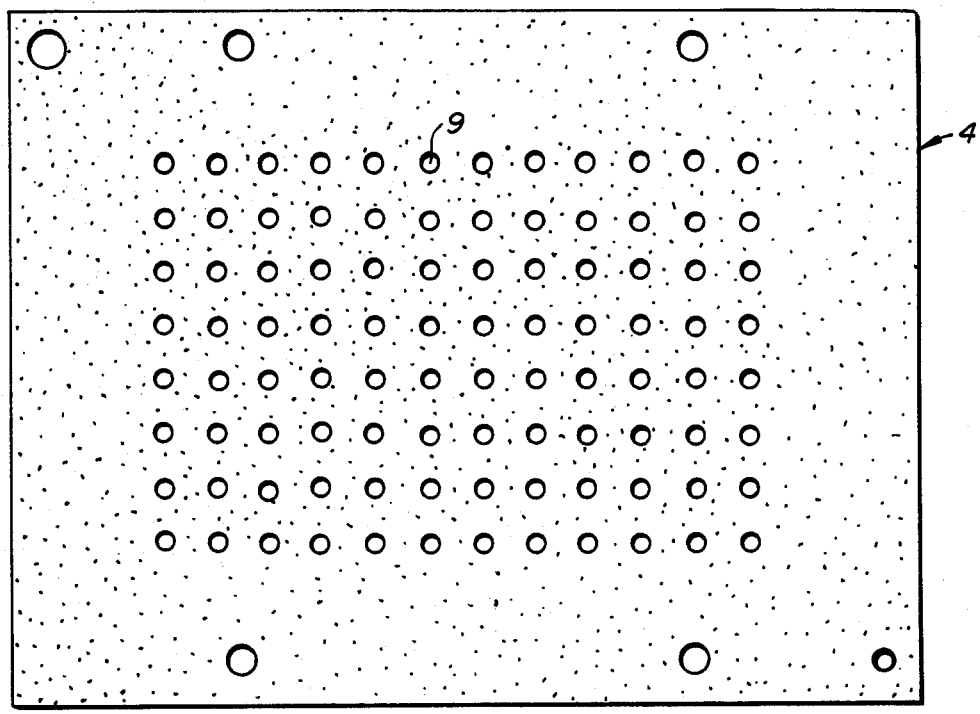
FIG. 3 is a plan view of a gasket for use in the embodiment of FIG. 1.

The gasket 4 is illustrated in FIG. 3, and can be formed of any deformable resilient inert material capable of forming a seal. Examples of such materials are silicon rubber, polyurethane elastomer and polyvinyl chloride. The thickness of the gasket is not critical, provided only that it is sufficient to form a seal, yet not so great as to cause substantial flow of the gasket material into the plate apertures upon compression. Typical gasket thicknesses will usually range from about 0.1 to about 0.5 cm. The gasket contains a rectangular array of apertures 9, to match in both diameter and location the openings at the bottom of the upper template.

Figure 4B:
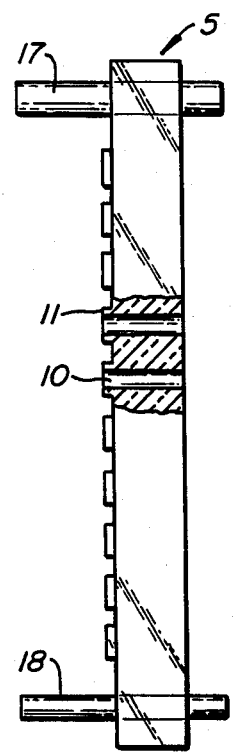
FIG. 4A is a plan view and FIG. 4B is an end view of a lower template for use in the embodiment of FIG. 1.
Figure 4A:
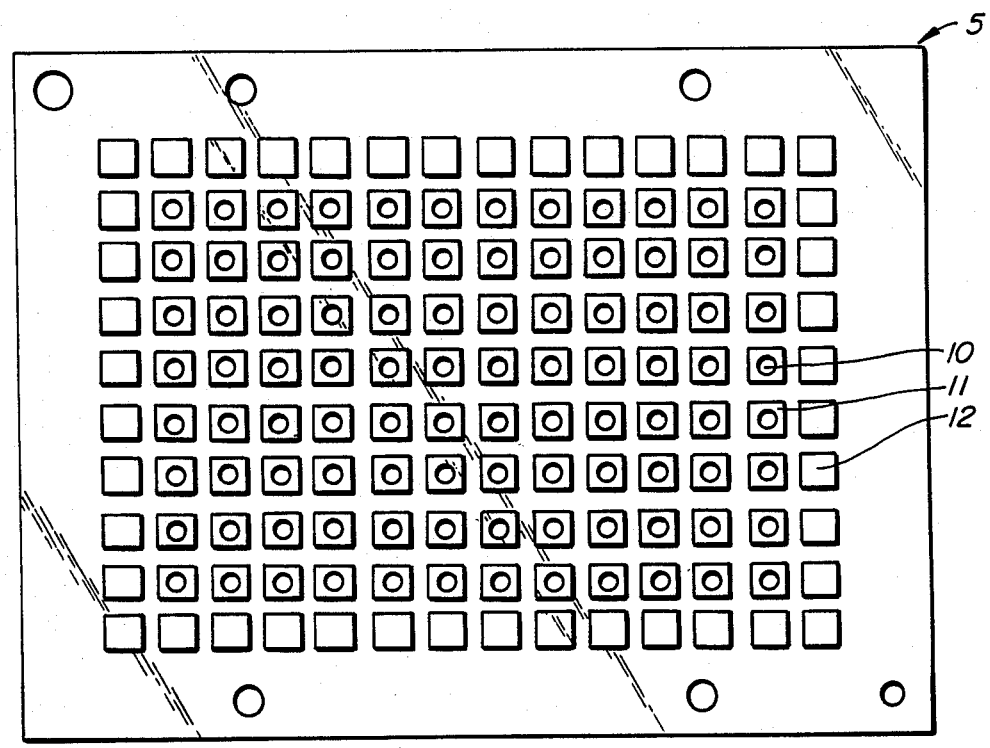

The lower template is illustrated in FIG. 4, and contains apertures 10 which, like those of the gasket 4, match the apertures of the upper template 2. The result of the matched apertures in the two templates and gasket is a continuous channel of constant diameter extending from the reduced diameter portion of the upper template on downward, through and out the bottom of the lower template, interrupted only by the microporous membrane. This leaves a series of clearly defined areas on the membrane corresponding to each of the 96 wells, the areas being uniform in size, each being the sole region of exposure to fluids passing through the plate assembly.

The lower template further contains bosses 11 extending upward from the plate, surrounding each aperture. The upper surface of each boss is flat and coplanar with each of the remaining bosses, to produce an even and concentrated pressure on the gasket when the plates are secured together, thus forming a complete seal around each aperture. The bosses shown in the figure are square in shape as a matter of manufacturing convenience.

As a further preferred embodiment, an extra ring of square protuberances 12 is included around the periphery of the 8-by-12 aperture array. These are identical to the central bosses except for the absence of an aperture at the center of each. These protuberances help to flatten the gasket and prevent warping of the gasket around the outermost apertures. This helps to ensure even and uniform sealing at the base of each well. This outer ring of protuberances is shown in the drawing as a segmented ring merely as a matter of manufacturing convenience. In an alternative arrangement, the outer ring could take the form of a continuous non-segmented ring encircling the 96-well array. The latter structure is more convenient when the template is formed by a molding process.

Figure 5A:
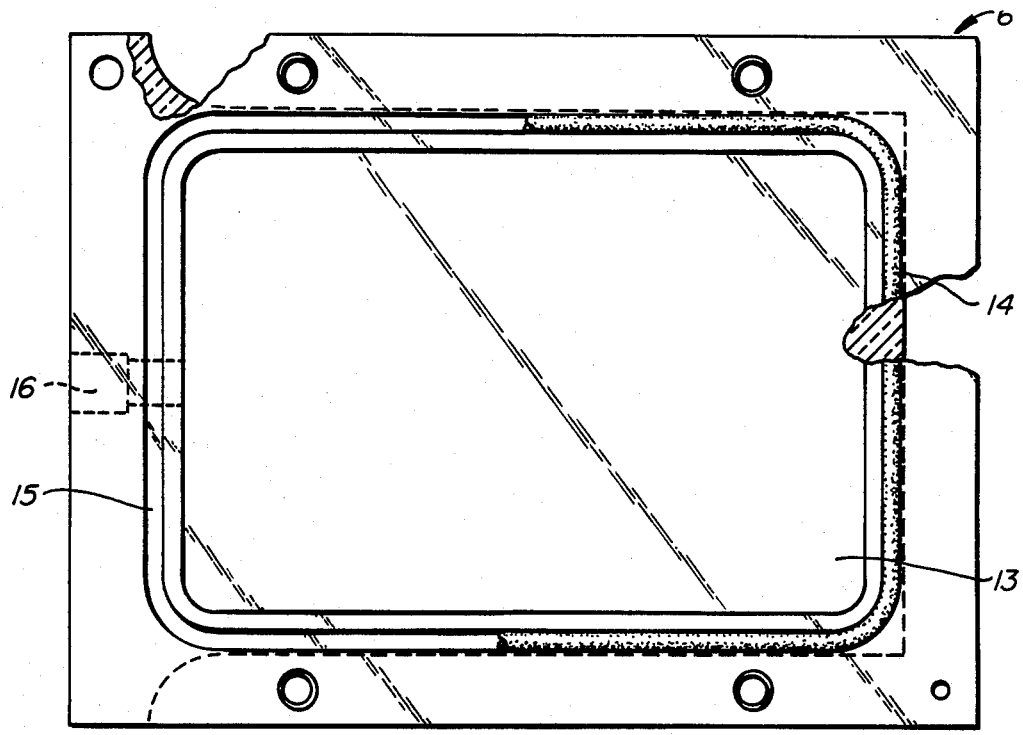
FIG. 5A is a plan view and FIG. 5B is an end view of a base plate for use in the embodiment of FIG. 1.
Figure 5B:
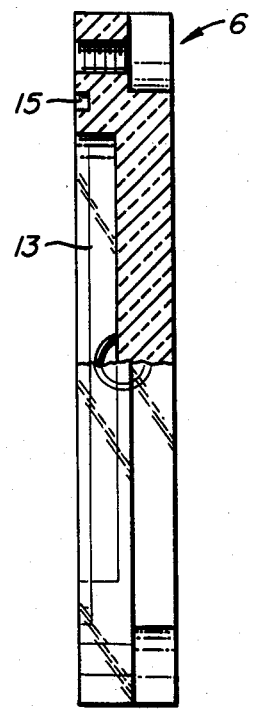

The base plate, as illustrated in FIG. 5, contains a central recess 13, which defines an enclosed chamber when the base plate 6 is joined with the lower template 5. The recess is sized and positioned so that all 96 wells will discharge into the chamber.

The assembly is designed to form an air-tight seal around the chamber when the assembly is secured together. This is readily achieved by placing an O-ring 14 around the recess 13. A groove 15 in the base plate facilitates the placement and use of the O-ring.

A port 16 is placed on one side of the base plate, leading to a vacuum line, not shown. A valve on the line, also not shown, permits the connecting and disconnecting of a vacuum for use of the assembly in performing either a filter assay or a static blot assay, respectively.

In the preferred construction of the plate assembly of the present invention, guides are included for ensuring proper alignment of the apertures and correct assembly of the various parts. In the embodiment shown in the drawings, these guides are shown as posts or dowel pins, two in number and of differing diameters. The dowel pins are designated 17 and 18, respectively, and are positioned in two diagonally opposed corners of the assembly. For convenience, each dowel pin is fused or press-fit in the lower template, with portions extending both above and below, to match close fitting holes in the upper template, gasket and base plate. The holes have differing diameters to match those of the dowel pins, with a fit close enough to ensure proper alignment, yet with sufficient clearance to permit easy assembly and removal.

The various components of the test plate assembly are secured together in any conventional manner. In the embodiment shown in the drawings, four captive manually operated screws 19 are incorporated into the structure for this purpose.

The plates themselves may be constructed of any rigid inert material, preferably transparent so that fluid motion and transfer can be observed. Conventional materials will suffice, notably acrylic, polycarbonate, polypropylene, polysulfone, etc.

The test plate assembly of the present invention may be used for either of two basic modes of operation—forcibly drawing a fluid through the membrane, and retaining a fluid above the membrane for a prolonged period of time. These functions may be used either individually or sequentially to serve in a wide variety of biochemical laboratory procedures. The flow-through mode of operation is useful, for example, in procedures involving contact between mobile and immobile species, where the latter is either covalently bound to the membrane or unable to penetrate it (as, for example, due to its larger size) and the former is suspended in the fluid in the well above the membrane. To draw the fluid through the membrane, a vacuum line is connected to vacuum port 16, drawing a vacuum on the enclosed chamber formed by the lower template 5 and the central recess 13 in the base plate 6. The static mode of operation is useful, for example, in procedures requiring the prolonged contact of two or more reactants in the fluid phase to form a complex. Once the reaction is complete, the difference in size between the complex and the unreacted species permits the complex to be separated out by filtration by converting to the flow-through mode described above. Further examples of static operation are those involving cell growth and the secretion of cellular products such as antibodies into a surrounding fluid. The secreted products may then be removed by flow-through operation. For the static mode no vacuum is applied; instead, the vacuum port 16 is sealed off, providing an entrapped blanket of air in the enclosed chamber sufficient to suspend the fluid or suspension in the wells indefinitely. In this way, the device can be switched from one mode to the other by merely operating the vacuum valve.

Th foregoing description is offered primarily for purposes of illustration. While a variety of embodiments have been disclosed, it is not intended that the present invention be limited to the particular structures and methods of operation set forth above. It will be readily apparent to those skilled in the art that numerous modifications and variations not mentioned here can still be made without departing from the spirit and scope of the invention as claimed herein below.

What is claimed is:

1. A biochemical test plate assembly for use in both filter assays and static blot assays, said assembly comprising:
    an upper planar template having upper and lower surfaces and containing a plurality of discrete apertures communicating an array of openings in said upper surface with an array of openings in said lower surface,
    a microporous film underlying said upper template and having dimensions sufficiently large to encompass said array of openings in the lower surface of said upper template,
    a gasket underlying said microporous film, having dimensions sufficiently large to encompass said array of openings in the lower surface of said upper template, and having an array of discrete apertures in alignment with said lower surface openings of said upper template,
    a lower planar template underlying said gasket, having an array of discrete apertures in alignment with said lower surface openings of said upper template, each of said apertures terminating at its upper end in a flat boss extending upward from said lower template, the uppermost surfaces of said bosses being coplanar and parallel to said lower template,
    a base plate underlying said lower template having a central recess of dimensions sufficiently large to encompass said array of apertures in said lower template, said recess defining an enclosed chamber below said lower template,
    means for forming a substantially air-tight seal around said enclosed chamber between said lower template and said base plate,
    means for securing said upper template, film, gasket, lower template and base plate together to seal said gasket against said bosses, and
    means for applying a vacuum to said enclosed chamber.

2. A biochemical test plate assembly according to claim 1 wherein all said apertures are cylindrical and of uniform size and spacing.

3. A biochemical test plate assembly according to claim 1 wherein the apertures in said upper template each have a tapering portion whereby the areas of said upper surface openings exceed those of said lower surface openings.

4. A biochemical test plate assembly according to claim 3 wherein the apertures in said upper template further comprise a constant cross-section portion between said tapering portion and said lower surface openings.

5. A biochemioal test plate assembly for use in both filter assays and statio blot assays, said assembly comprising:
    an upper planar template having upper and lower surfaces and containing a plurality of discrete apertures of circular cross section communicating an array of circular openings in said upper surface with an array of circular openings in said lower surface, the openings in each said array being of uniform size and spacing, and each said aperture having a tapering portion and constant diameter portions above and below said tapering portion,
    a microporous film underlying said upper template and having dimensions sufficiently large to encompass said array of openings in the lower surface of said upper template, a gasket underlying said microporous film, having dimensions sufficiently large to encompass said array of openings in the lower surface of said upper template, and having an array of discrete apertures in alignment with said lower surface openings of said upper template, a lower planar template underlying said gasket, having an array of discrete apertures in alignment with said lower surface openings of said upper template, each of said apertures terminating at its upper end in a flat boss extending upward from said lower template, the uppermost surfaces of said bosses being coplanar and parallel to said lower template, a base plate underlying said lower template having a central recess of dimensions sufficiently large to encompass said array of apertures in said lower template, said recess defining an enclosed chamber below said lower template, means for forming a substantially air-tight seal around said enclosed chamber between said lower template and said base plate, means for securing said upper template, film, gasket, lower template and base plate together to seal said gasket against said bosses, and means for applying a vacuum to said enclosed chamber.

* * * * *